(12) United States Patent
McCombe

(10) Patent No.: US 10,045,856 B2
(45) Date of Patent: Aug. 14, 2018

(54) METHOD OF REDUCING LOADING FAILURE FOR A PROSTHETIC COMPONENT

(75) Inventor: Peter McCombe, Brisbane (AU)

(73) Assignee: Nuvasive, Inc., San Diego, CA (US)

( * ) Notice: Subject to any disclaimer, the term of this patent is extended or adjusted under 35 U.S.C. 154(b) by 1295 days.

(21) Appl. No.: 12/084,471

(22) PCT Filed: Nov. 2, 2006

(86) PCT No.: PCT/AU2006/001640
§ 371 (c)(1),
(2), (4) Date: Sep. 14, 2010

(87) PCT Pub. No.: WO2007/051247
PCT Pub. Date: May 10, 2007

(65) Prior Publication Data
US 2010/0331982 A1    Dec. 30, 2010

(30) Foreign Application Priority Data
Nov. 4, 2005   (AU) ................................ 2005906204

(51) Int. Cl.
*A61F 2/44*   (2006.01)
*A61F 2/30*   (2006.01)

(52) U.S. Cl.
CPC ........ *A61F 2/4425* (2013.01); *A61F 2/30734* (2013.01); *A61F 2002/30159* (2013.01); *A61F 2002/30172* (2013.01); *A61F 2002/30649* (2013.01); *A61F 2230/0028* (2013.01); *A61F 2230/0052* (2013.01)

(58) Field of Classification Search
CPC .......... A61F 2/4425; A61F 2002/30649; A61F 2/4465
USPC .............................. 623/17.11–17.16; 606/279
See application file for complete search history.

(56) References Cited

U.S. PATENT DOCUMENTS

| | | | | |
|---|---|---|---|---|
| 5,258,031 A | * | 11/1993 | Salib | A61F 2/4425 606/247 |
| 5,425,773 A | * | 6/1995 | Boyd | A61F 2/4425 623/17.15 |
| 5,676,701 A | * | 10/1997 | Yuan | A61L 27/045 606/247 |
| 5,888,226 A | | 3/1999 | Rogozinski | |
| 6,679,915 B1 | * | 1/2004 | Cauthen | A61B 17/1671 623/17.11 |
| 6,706,068 B2 | | 3/2004 | Ferree | |
| 7,503,935 B2 | * | 3/2009 | Zucherman et al. | 623/17.15 |

(Continued)

FOREIGN PATENT DOCUMENTS

WO    WO2005051243    *  6/2005   ............... A61F 2/44

*Primary Examiner* — Jan Christopher Merene
*Assistant Examiner* — Atiya Mahmud

(57) ABSTRACT

A method for reducing prosthetic loading failure including the steps of providing a prosthesis for a vertebral column comprising at least an upper part for attachment to an upper vertebrae and a lower part for attachment to a lower vertebrae, the upper part having a lower curved surface and the lower part having an upper curved surface, wherein the upper and lower curved surfaces have a center of radius of curvature offset rearwardly with respect to a central vertical axis through the upper and lower vertebrae, and positioning the centroid of at least one of the upper and lower parts substantially on the same vertical axis of the center of radius of curvature.

9 Claims, 5 Drawing Sheets

(56) References Cited

U.S. PATENT DOCUMENTS

| | | | |
|---|---|---|---|
| 7,887,589 B2* | 2/2011 | Glenn | A61F 2/4425 |
| | | | 623/17.14 |
| 2004/0199251 A1 | 10/2004 | McCombe et al. | |
| 2005/0043802 A1* | 2/2005 | Eisermann et al. | 623/17.16 |
| 2005/0055098 A1* | 3/2005 | Zdeblick | A61B 17/1671 |
| | | | 623/17.11 |
| 2005/0149188 A1 | 7/2005 | Cook et al. | |
| 2005/0283242 A1* | 12/2005 | Zucherman et al. | 623/17.15 |
| 2006/0036325 A1* | 2/2006 | Paul et al. | 623/17.14 |
| 2006/0069437 A1* | 3/2006 | Weber | 623/17.14 |
| 2006/0095132 A1* | 5/2006 | Kirschman | 623/17.14 |
| 2006/0259147 A1* | 11/2006 | Krishna et al. | 623/17.15 |
| 2009/0082867 A1* | 3/2009 | Sebastian Bueno et al. | 623/17.16 |

\* cited by examiner

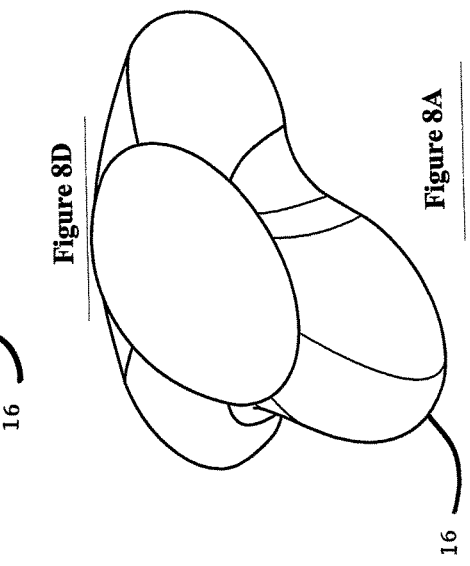
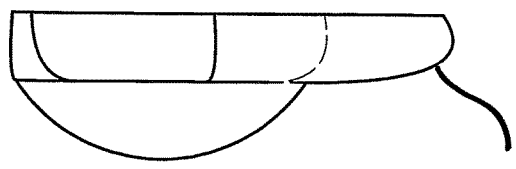
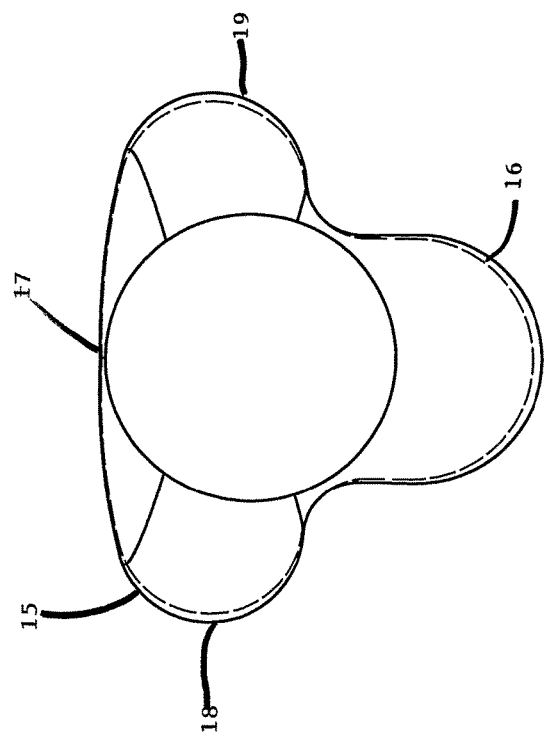
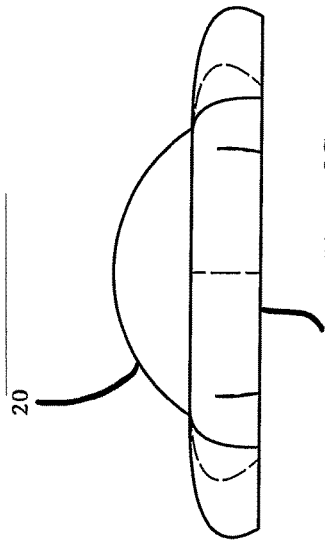

METHOD OF REDUCING LOADING FAILURE FOR A PROSTHETIC COMPONENT

FIELD OF THE INVENTION

The present invention relates to a prosthesis for use in a skeletal structure. In one application the invention relates to a prosthesis for use as an artificial invertebral disk, predominantly but not exclusively for use in human spines.

BACKGROUND OF THE INVENTION

A human invertebral disk maintains a linkage between adjacent vertebrae of the vertebral column. It must fulfil a number of important functions including load bearing and dampening of impact forces. Furthermore, it must permit a complex pattern of movements and resist various stresses, pure or combined, in the sagittal, coronal and axial planes. Assisted by musco-ligamentous structures surrounding the spine, the invertebral disk must also help to maintain the normal alignment of the vertebrae of the spinal column.

An ideal artificial disk replacement will accurately reproduce all the functions of the invertebral disk. However although there have been many different artificial disks which have been described and tested, at this time they have all failed to reproduce the abilities of an invertebral disk.

Typical failings of previous artificial disks have included loosening or dislodgement of vertebral fixation, premature materials wear or structural failure, poor replication of normal or physiological spinal segmental motion and predisposition to the loss of normal neutral vertebral alignment.

An important aspect of the normal motion of the spinal column and the kinematics of the various invertebral motion segments is the behaviour of the motion segments during flexion and extension movements in the sagittal plane. Fundamental to the kinematics is the location of the instantaneous axis of rotation (IAR). The IAR varies from level to level within the spinal column and throughout flexion and extension movements for any given motion segment (level).

One type of spinal disk prosthesis is described in U.S. Pat. No. 5,674,296. The endoprosthesis described consists of a resilient body having a generally elliptical shape. The endoprosthesis is affixed between adjacent upper and lower vertebrae through L-shaped supports each having confronting concave-convex legs for engaging the adjacent bone sectional thickness on one surface and retaining the resilient endoprosthesis therebetween. The endoprosthesis is centrally located between the upper and lower vertebrae to allow central pivoting of the upper vertebrae relative to the lower vertebrae.

In addition to the above a gasket and seal are located at the anterior and posterior regions between the vertebrae to seal the endoprosthesis in its position between the upper and lower vertebrae.

U.S. Pat. No. 5,556,431 describes another type of invertebral disk endoprosthesis in which top and bottom plates are used instead of the L-shaped supports of the above identified US patent. The endoprosthesis described includes a core which has spherical upper and lower surfaces which from drawings shown appear to be aligned with a central vertical axis through the upper and lower vertebrae.

In contrast to U.S. Pat. No. 5,674,296 the prosthesis core of this patent has an edge rim which limits the range of movement of the core and ensures even under extreme conditions cohesion of the prosthesis.

This patent also discloses displacement of the centre of articulation of the prosthesis towards the rear relative to the centre of the vertebral end plates so as to provide sufficient space in the ventral edge area of the prosthesis upper and lower plates so as to enable receipt of bone screws.

Other artificial prostheses have sought to reproduce normal variation in the location of the IAR using various mechanisms including the use of visco-elastic deformable cores. An example of this is shown in U.S. Pat. No. 5,824,094. Unfortunately these type of artificial disks are subject to premature materials wear and stress failure. Furthermore, artificial disks with metallic springs have not yet found their way into clinical use.

All of the artificial disks described above have inherent problems which ultimately create unnatural stresses and resultant pain for an artificial disk implant recipient. The present invention provides an alternative prosthesis which is aimed at mitigating at least some of the problems associated with prior art prosthesis.

The applicant's co-pending application identified by application number 2005901682 and entitled A Prosthesis is incorporated herein by way of reference.

A prosthesis is described in this patent application comprising an upper part for attachment to an upper vertebrae, a lower part for attachment to a lower vertebrae and a middle part located between the upper and lower parts. The centre of the radius of curvature of co-acting surfaces of all parts is offset rearwardly with respect to a central vertical axis through the upper and lower vertebrae.

The upper part which is in the form of an upper end plate typically has an upper surface which is connected to the lower surface of an upper vertebrae. Investigations have revealed that the upper end plate may suffer from subsidence. Typically plate failure occurs by tilting with the posterior aspect of the prosthesis subsiding. The anterior aspect has not been shown to subside. Furthermore, subsidence occurs almost exclusively at the upper posterior corner of the upper plate.

SUMMARY OF THE INVENTION

According to the present invention there is provided a method of reducing loading failure for a prosthetic component such as an upper end plate. The method may also be applicable to a lower end plate.

According to one aspect of the present invention there is provided a method for reducing prosthetic loading failure including the steps of providing a prosthesis for a vertebral column comprising at least an upper part for attachment to an upper vertebrae and a lower part for attachment to a lower vertebrae, the upper part having a lower curved surface and the lower part having an upper curved surface, providing the upper and lower curved surfaces with a centre of radius of curvature offset rearwardly with respect to a central vertical axis through the upper and lower vertebrae, and positioning the centroid of at least one of the upper and lower parts substantially on the same vertical axis of the centre of radius of curvature.

Preferably the method includes the step of positioning the centroid of a contact surface of at least one of the upper and lower parts substantially on the same vertical axis as the centre of the radius of curvature, which contact surface contacts an adjacent vertebrae.

Preferably the prosthesis includes a middle part which is able to pivot and translate with respect to the upper and lower parts.

According to another aspect of the present invention there is provided a prosthesis for a skeletal body comprising an upper surface and a lower surface, with one of the surfaces being a contact surface configured to contact an adjacent surface of a skeletal body part, the contact surface having a centroid located substantially vertically aligned with the centre of rotation of curvature of the prosthesis.

Preferably the prosthesis is offset with respect to a central vertical axis through upper and lower skeletal body parts.

The prosthesis may comprise an end plate for attachment to a skeletal body part.

The prosthesis preferably comprises an upper or lower end plate for attachment to a skeletal body part.

The prosthesis may comprise an insert configured for location between an end plate and a skeletal body part.

The skeletal body part may be a vertebrae.

It is preferred that a skeletal body includes any skeletal structure for a biological or mechanical structure.

It is preferred that a prosthesis refers to any component which is designed to replace part of a skeletal structure, simulate or enhance movement of a skeletal structure.

According to another aspect of the present invention there is provided a method of reducing loading failure for a prosthetic component comprising; identifying the centre of the radius of curvature for a prosthesis, where the centre of the radius of curvature is offset from a central vertical axis through a skeletal structure, identifying a vertical axis through the centre of radius of curvature and configuring an upper prosthetic part or a lower prosthetic part with a centroid for its contact surface, which is located substantially on the central vertical axis when in situ.

According to a further aspect of the present invention there is provided a method of reducing loading failure for a prosthetic component, comprising identifying the centre of rotation of curvature for a prosthesis, identifying an equivalent location for the centre of rotation of curvature on a contact surface of an upper or lower prosthetic part, which contact surface is configured to be fixed to a skeletal part and configuring the contact surface with a centroid substantially at the equivalent location for the centre of rotation of curvature.

Preferably the step of configuring includes configuring a surface of the skeletal part which is the surface to which the contact surface is attached.

The step of configuring preferably includes designing, manufacturing, producing, engineering and any equivalent action which results in a contact surface with a centroid located substantially at the equivalent location.

The method may include the step of providing a prosthesis comprising at least two parts including an upper part and lower part which are able to pivot with respect to each other when in use.

The method may also include providing a prosthesis with a core which is able to pivot and/or translate with respect to the upper and lower parts.

The upper part may be able to slide (translate with respect to the upper part).

The upper or lower prosthetic part may comprise an insert.

The upper or lower prosthetic part preferably comprises an end plate and/or an insert.

The insert may be configured to build up a relevant portion of an upper surface of an upper part or a lower surface of a lower part.

The contact surface may comprise an upper surface of the upper part or a lower surface of the lower part.

The method may include cutting out a part of the contact surface.

The method may include removing a portion of the contact surface.

The configuring step may include providing the contact surface with a recessed region.

Preferably the recessed region is located between opposite sides of the contact surface.

The method may include cutting out a portion in front of the centroid.

The method may include creating a recess between opposite sides of an anterior portion of the upper surface.

Preferably the method includes forming substantially identical side portions which are separated by a recess.

The recess may be rectangular in shape.

The side portions may have substantially parallel edges.

The side portions may have a generally rectangular cross section.

The anterior portion may comprise a plurality of recesses or holes.

It is preferred that according to at least one of the above aspects of the invention that if subsidence is to occur for an upper end plate in a prosthesis, that it occurs without tilting and is parallel subsidence.

According to one aspect of the present invention there is provided a method of reducing load failure for a prosthetic component, comprising identifying the centre of rotation of curvature for a prosthesis, identifying an equivalent location for the centre of rotation of curvature on a contact surface of an upper or lower prosthetic part, which contact surface is configured to be fixed to a skeletal part and configuring the contact surface with a centroid which is moved towards the equivalent location for the centre of rotation of curvature.

Although it is desirable to configure the contact surface with a centroid substantially at the equivalent location for the centre of rotation of curvature, a reduction in loading failure can be achieved by any movement of the centroid towards the vertical axis which would align with the centre of rotation of curvature of the skeletal part.

Preferably the method includes removing part of the prosthetic component in a manner which moves the centroid towards a position which is closer to the centre of rotation of curvature.

It is preferred that the method includes creating a recess between opposite sides of an anterior portion of an upper surface of at least one of the upper and lower prosthetic parts.

BRIEF DESCRIPTION OF THE DRAWINGS

A preferred embodiment of the present invention may now be described by way of example only with reference to the accompanying drawings in which:

FIG. 8A shows a perspective view of an end plate insert for use with a lower plate prosthesis according to one embodiment of the present invention;

FIG. 8B shows a top view of the end plate insert shown in FIG. 8A;

FIG. 8C shows a front view of the end plate insert shown in FIG. 8A;

FIG. 8D shows an end view of the end plate insert shown in FIG. 8A;

DETAILED DESCRIPTION OF THE DRAWINGS

According to a preferred embodiment of the present invention the instant centre of rotation (ICR) needs to be in the posterior portion of the upper end plate of the inferior vertebral body. Failure to achieve this position will prevent normal movement of the prosthesis and facet movement will be abnormal.

Little attention has so far been given to the statically loaded disc prosthesis—in other words, when it is not moving. This is the position in which the implant finds itself most of the time. In this position the neuromuscular control system recruits whatever muscles are necessary to maintain a static posture.

Figure 1:
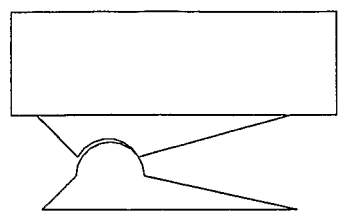
FIG. 1 shows a side schematic view of a prosthesis.

In a situation where a person is standing in a static position, the upper and lower end plates are parallel (FIG. 1).

Figure 2:
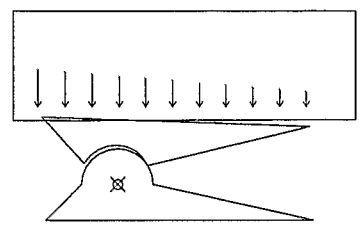
FIG. 2 shows the prosthesis shown in FIG. 1 with a non-uniform pressure distribution.

If it is assumed that the applied load is distributed evenly across the surface of the implant it will have a uniform pressure distribution. If this were the case with the standard maverick footprint there would be an unbalanced net moment causing the prosthesis to tilt into flexion and subside at the posterior end plate. This can be conceptually thought about by considering a series of small areas of the prosthesis end plate. If the pressure distribution is uniform, the force on these small areas is equal. The moment about the pivot point of the prosthesis however depends on the distance of that small area from the pivot. If all the moments are summed together there will be a net flexion moment. Another way of considering this is that the centre of mass of the current maverick prosthesis is in front of the pivot point, thus causing a net moment. This will make the pressure distribution non uniform. A non uniform pressure distribution would make the prosthesis fail by subsidence into the posterior end plate (FIG. 2).

To deal with the above problem the upper end plate has been designed with a sufficient amount of the surface area removed from the front of the prosthesis so that the net moment is nil. This results in a substantially uniform pressure distribution.

Figure 3:
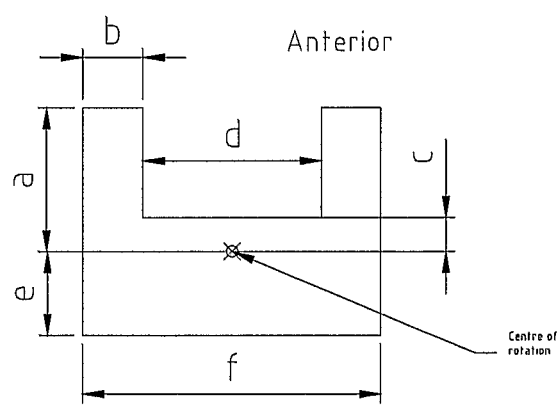
FIG. 3 shows a top view of a top plate of a prosthesis according to a preferred embodiment of the present invention.
Figure 4:
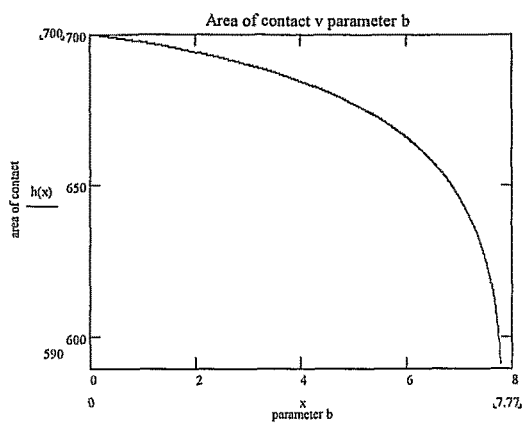
FIG. 4 shows a graphical representation of parameter b in FIG. 3 versus surface area.

FIG. 3 shows an embodiment of the invention in which the upper surface of the upper end plate has a rectangular "cut out" from the front of a maverick end plate.

Figure 7:
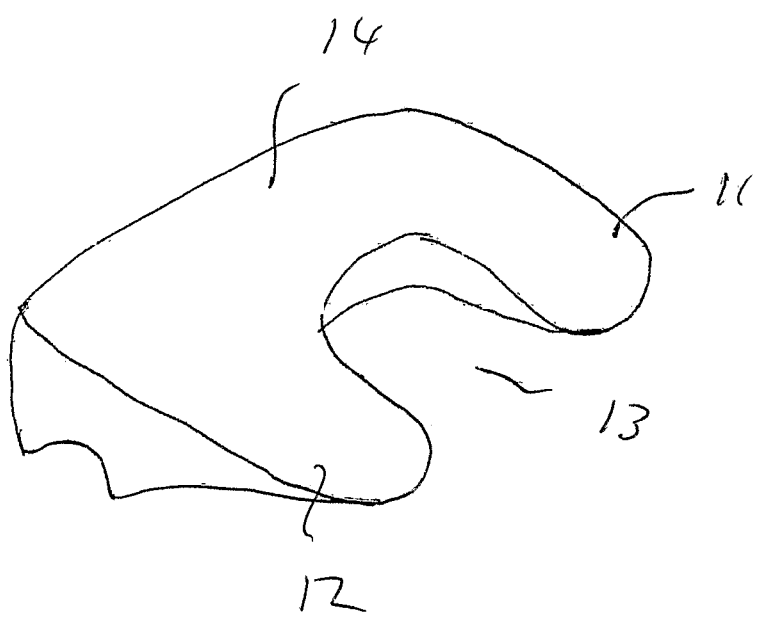
FIG. 7 shows a perspective view of an upper end plate of a prosthesis according to one embodiment of the present invention.

As shown the area which has been removed is generally rectangular in shape and as shown more clearly in FIG. 7 comprises anterior lobes 11, 12 with a space 13 therebetween. The posterior region of the prosthesis remains substantially the same as an existing prosthesis upper end plate. Likewise the lower surface has a lower centre of radius of curvature in accordance with requirements of an earlier designed prosthesis.

For a pure mathematical analysis of the effects of removing surface area from the anterior region of the prosthesis, it is necessary to consider a uniform pressure distribution acting on the entire surface area. At each small area a uniform force will act.

Referring to first principles a mathematical analysis can be provided for the prosthesis as shown in FIG. 3 on the basis that moments are balanced around the pivot line.

Thus moments acting behind the pivot equal moments acting in front of the pivot.

The resultant mathematical equation is as follows:

$$\int_0^a \int_0^{2b} Fy \cdot dxdy + \int_0^c \int_0^{f-2b} Fy \cdot dxdy = \int_0^e \int_0^f Fy \cdot dxdy \quad (1)$$

$$\int_0^{2b} \left[\frac{Fy^2}{2}\right]_0^a dx + \int_0^{f-2b} \left[\frac{Fy^2}{2}\right]_0^c dx = \int_0^f \left[\frac{Fy^2}{2}\right]_0^e dx$$

$$\int_0^{2b} \frac{Fa^2}{2} dx + \int_0^{f-2b} \frac{Fc^2}{2} dx = \int_0^f \frac{Fe^2}{2} dx$$

$$\left[\frac{Fa^2 x}{2}\right]_0^{2b} + \left[\frac{Fc^2 x}{2}\right]_0^{f-2b} = \left[\frac{Fe^2 x}{2}\right]_0^f$$

$$\frac{Fa^2 \cdot 2b}{2} + \frac{Fc^2 \cdot (f-2b)}{2} = \frac{Fe^2 \cdot f}{2}$$

$$2a^2 b + c^2(f-2b) = e^2 f$$

$$c^2(f-2b) = e^2 f - 2a^2 b$$

$$c^2 = \frac{e^2 f - 2a^2 b}{(f-2b)}$$

$$c = \sqrt{\frac{e^2 f - 2a^2 b}{(f-2b)}}$$

as parameters a, e and f are fixed by the dimensions of the current maverick prosthesis equation 1 gives the relationship between c and b that will result in a number of solutions that still will have balanced moments. The total area of contact will vary according to the equation.

area=ef+2ab+cd

Using a reasonable estimate for parameter 'b' of 7 mm the shape in FIG. 14 was submitted for engineering subsidence testing against a sawbone foam.

The centre of mass in the y axis for the above diagram is calculated as 10.6 mm from the posterior edge of the prosthesis using the formula.

$$\frac{\sum Mo}{\sum a}$$

where Mo=Moment and a=area

This suggests also that the prosthesis should not tilt when loaded.

It was theorized also that whilst the yield load should be decreased because of the reduction in surface area that to some extent this would be compensated for by the avoidance of high loading on the posterior edge of the prosthesis due to non uniform pressure distribution. This would be confirmed by a finding of a lower percentage reduction in failure load than would be expected by the reduction in surface area alone.

Preliminary testing by compressing a maverick disc prosthesis into soft foam suggested that tilting did occur and was associated with a translatatory movement.

The load displacement characteristics of the standard maverick disc were tested against sawbone material using a roller bearing to allow lateral displacement and to compare the results with at least a machined surface of the shape shown in FIG. 15.

Experimental results revealed the following:

1. Under loading conditions that did not allow the upper end plate to flex in relation to the lower end plate the Maverick disc prosthesis collapsed into an attitude of flexion by subsiding into the posterior end plate.

2. The anterior edge of the prosthesis did not contact the sawbone and indentation appeared to stop 10 mm in front of the ball (equal to the distance of the ball from the posterior edge).

3. The area of modified cutout prosthesis was 69% of the area of the original maverick prosthesis. While the Yield load was 89% of the original.

4. Subsidence by tilting of the unmodified prosthesis was associated with 2 mm of posterior displacement of the lower vertebrae in relation to the fixed upper vertebrae. This would cause extra facet loading.

5. The modified cutout prosthesis did not tilt with subsidence and collapsed into the end plate with its end plate parallel to the sawbones end plate. This was accomplished with very little lateral displacement (0.15 mm).

Figure 5:
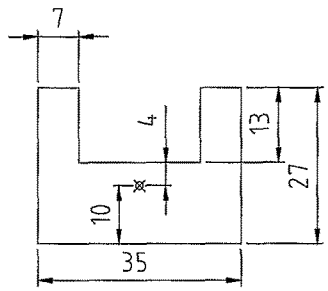
FIG. 5 shows a top view of a proposed cut out for testing that has net moment of zero.
Figure 6:
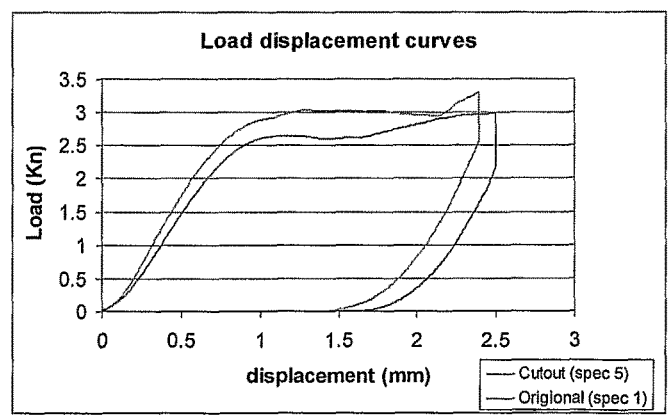
FIG. 6 shows a comparison of load displacement curves for an unmodified prosthesis and a prosthesis as shown in FIG. 5.

FIG. 6 shows a comparison of load displacement graphs of an unmodified prosthesis compared to a modified prosthesis as shown in FIG. 5. From this comparison the following observations can be made.

1. The peripheral strength and relative weakness of the central portion of the end plate mean that if an anterocentral cutout is made it should cause less reduction in total end plate yield than if the material was uniform. This may enlarge the discrepancy between yield load achieved and that expected by reduction in surface area alone.

2. The posterior end plate is stronger than the anterior end plate. The centre of mass of the prosthesis may therefore not need to be exactly at the axis of rotation of the prosthesis and therefore the cutout may need to be less.

3. By adding more lateral area near the pivot point the surface area of contact could be increased with little effect on the net moments. A more rounded prosthesis would also have a centre of mass closer to the pivot point. The vertebral end plate is known to be in the shape of a cardioid[2].

4. The effect of cyclical loading is not known. It is possible that it is significant with high cyclical loads at the posterior edge of the prosthesis and the effect noted above may be exaggerated.

Based on the above it is considered that in addition to redesigning the upper surface of the upper end plate an alternative strategy may be to provide an insert plate configured to move the centroid of the combined end plate and insert. According to another embodiment of the invention a lower end plate may be provided with an insert plate to avoid redesigning the lower surface.

FIGS. 8A to 8D show one embodiment of the lower end plate which has a central spherical region 20 which couples with an upper end plate having a similarly shaped recess (socket) formed in its lower surface. This insert plate would be attached to the adjacent vertebrae. The posterior region 16 of the plate 15 would effectively cover the majority of the posterior section of the lower end plate and the anterior region 17 would be provided with side lobes 18 and 19 to effectively build up the sides of the lower end plate. The result would be an effective recess being formed between the anterior sides of the lower end plate. This would result in effective movement of the centroid for the lower end plate towards the centre of rotation of curvature of the prosthesis.

FIGS. 9A to 9D show an alternative embodiment of a lower end plate 30 which is generally more rectangular in shape than the previous embodiment. Underneath the insert plate a scalloped out region 31 is provided anteriorly with its centre aligned with the centre of the semi-spherical ball portion 32 on its upper surface.

Figure 9D:
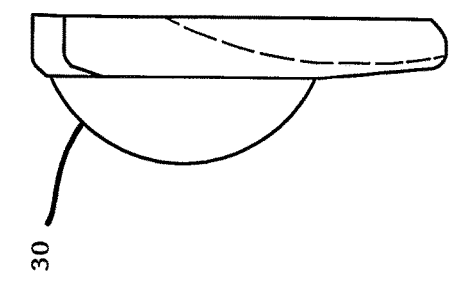
FIG. 9D shows an end view of the end plate insert shown in FIG. 9A.
Figure 9A:
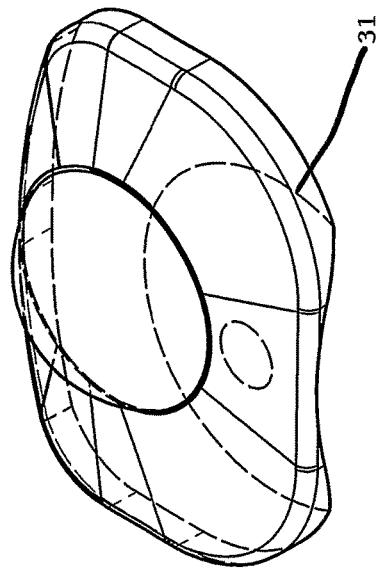
FIG. 9A shows a perspective view of an end plate insert according to a further embodiment of the present invention.
Figure 9B:
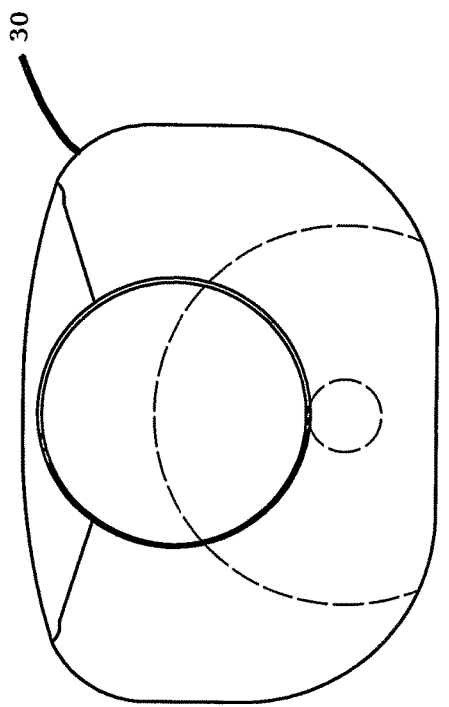
FIG. 9B shows a top view of the end plate insert shown in FIG. 9A.
Figure 9C:
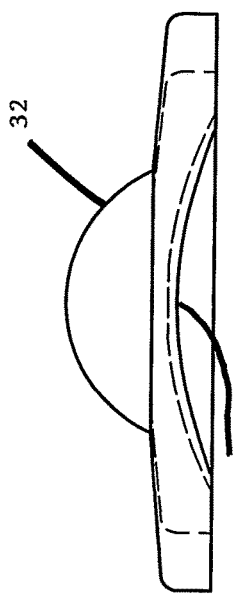
FIG. 9C shows a front view of the end plate insert shown in FIG. 9A.

As shown in FIGS. 9A and 9D the scalloped out region 31 commences at a forward most end of the insert and curves concavely rearwardly to the bottom surface more than half of the way along the length of the end plate (measured from front to rear) to a point which is rearward of the centre of the semi-spherical ball portion 32. This effectively moves the centroid rearwardly.

FIG. 9A shows that the scalloped region is part circular in shape.

Thus it can be seen that the embodiment shown in FIGS. 9A to 9D uses a scalloped out region to provide a change in the position of the centroid whereas the embodiment shown in FIGS. 8A to 8D achieves the same or a similar purpose by shaping the insert with side loads 18, 19.

The inserts shown in FIGS. 8A to 9D can be configured to couple with an upper end plate in a similar fashion to that shown in FIGS. 1 and 2. As the design of both of the embodiments shown in FIGS. 8A to 9D result in a change in the position of the centroid of the lower end plate, this can have advantages as outlined previously having regard to the previous experimental results.

According to an alternative embodiment of the invention the lower end of the adjacent vertebrae to the upper end plate may be physically altered so that a recess is provided in an anterior central section to provide a similar effect to that discussed above by providing a recess in the anterior central region of the upper end plate.

According to alternative aspects of the present invention the same theory relied upon may be applied to the lower end plate of a prosthesis.

It is to be understood that, if any prior art publication is referred to herein, such reference does not constitute an admission that the publication forms a part of the common general knowledge in the art, in Australia or in any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for reducing prosthetic loading failure including the steps of:
   (a) providing a prosthesis for placement within a disc space of a vertebral column, the prosthesis comprising
   (i) an upper part for attachment to an upper vertebra, the upper part ]having a lower endplate surface adjacent the disc space and an upper contact surface opposite the lower endplate surface for contacting an upper vertebra, said upper contact surface having a U-shape defined at an anterior portion by a pair of spaced anterior lobes separated by a central cutout that extends through the upper contact surface and lower endplate surface; and (ii) a lower part for attachment to a lower vertebra, the lower part having an upper endplate surface adjacent the disc space and a lower contact surface opposite the upper endplate surface for contacting a lower vertebra, the lower endplate surface of the upper part including a concave surface portion, the upper endplate portion of the lower part including a convex surface portion, wherein the concave surface portion of the upper part and the convex surface portion of the lower part are configured to pivot with respect to each other when in use; the concave surface portion being arranged on the upper part and the convex surface portion being arranged on the lower part such that the prosthesis has a centre of radius of curvature with a central vertical axis that is offset rearwardly with respect to a central vertical axis of the upper and lower vertebrae when the prosthesis is implanted in the disc space between the upper vertebra and lower vertebra; and (b) configuring the prosthesis such that the dimensions of the upper part cutout eliminate a sufficient amount of surface area from the anterior portion of the upper contact surface to define an upper contact surface that creates a generally balanced net moment anteriorly and posteriorly about the central vertical axis of the centre of radius of curvature when the prosthesis is implanted in the disc space between the upper vertebra and lower vertebra.

2. The method as claimed in claim 1, wherein the prosthesis is configured such that a centroid of the upper contact surface of the upper part is positioned substantially on the vertical axis passing through the centre of the radius of curvature when the prosthesis is implanted between the upper vertebra and lower vertebra.

3. The method as claimed in claim 2, wherein the upper contact surface of the upper part and the lower contact surface of the lower part are configured such that a portion of the prosthesis is offset posteriorly with respect to the central vertical axis of the upper and lower vertebrae.

4. The method as claimed in claim 1, wherein the prosthesis is configured such that a centroid of the lower contact surface of the lower part is positioned substantially on the vertical axis passing through the centre of the radius of curvature when the prosthesis is implanted between the upper vertebra and lower vertebra.

5. A method of reducing loading failure for a prosthetic component, comprising:
(a) providing a prosthesis for a vertebral column comprising at least (i) an upper part for attachment to an upper vertebra, the upper part having a lower endplate surface adjacent the disc space and an upper contact surface opposite the lower endplate surface for contacting the upper vertebra, said upper contact surface having a U-shape defined at an anterior portion by a pair of spaced anterior lobes separated by a central cutout that extends through the upper contact surface and lower endplate surface, and (ii) a lower part for attachment to a lower vertebra, the lower part having an upper endplate surface adjacent the disc and a lower contact surface opposite the upper endplate surface for contacting the lower vertebra, the lower contact surface having a shape defined at least in part by one of a recess and a scallop extending through an anterior portion of the lower contact surface, the upper part lower endplate surface having a concave surface portion and the lower part upper endplate surface having convex surface portion;

(b) identifying a centre of rotation of curvature for the prosthesis, wherein the centre of radius of curvature of the upper and lower surfaces has a central vertical axis that is offset rearwardly with respect to a central vertical axis of the upper and lower vertebrae during use; and (c) configuring the cutout and the recess or scallop such that the upper part upper contact surface and the lower part lower contact surface each have a centroid located posterior to the central vertical axis passing of the upper and lower vertebrae during use, wherein the cutout and the recess or scallop are dimensioned to eliminate a sufficient amount of surface area from the anterior portion of each of the upper contact portion and lower contact portion create a balanced net moment anteriorly and posteriorly about the vertical axis of the centre of radius of curvature when implanted during use.

6. The method as claimed in claim 5, wherein the scallop is a semi-circular scallop.

7. The method as claimed in claim 6, wherein the scallop is disposed at least in part on either side of the anterior-to-posterior midline of the lower part.

8. The method as claimed in claim 5, wherein the lower concave surface of the upper part and the upper convex surface of the lower part cooperate together to enable the upper part and lower part to articulate relative to one another when the prosthesis is in use implanted within an intervertebral space of a patient.

9. The method as claimed in claim 5, wherein the prosthesis further comprises a middle part which is able to pivot and translate with respect to the upper and lower parts.

* * * * *